(12) United States Patent
Korodi et al.

(10) Patent No.: US 6,995,277 B2
(45) Date of Patent: Feb. 7, 2006

(54) PROCESS FOR PREPARING SIMVASTATIN HAVING CONTROLLED RANGES OF SIMVASTATIN DIMER CONTENT

(75) Inventors: Ferenc Korodi, Debrecen (HU); Csaba Szabo, Debrecen (HU); Szabolcs Salyi, Debrecen (HU); Istvan Bodi, Balmazujvaros (HU)

(73) Assignee: Plus Chemicals, B.V., Mijdrecht (NL)

( * ) Notice: Subject to any disclaimer, the term of this patent is extended or adjusted under 35 U.S.C. 154(b) by 93 days.

(21) Appl. No.: 10/777,535

(22) Filed: Feb. 11, 2004

(65) Prior Publication Data

US 2004/0267044 A1 Dec. 30, 2004

Related U.S. Application Data

(60) Provisional application No. 60/446,764, filed on Feb. 11, 2003, provisional application No. 60/463,065, filed on Apr. 15, 2003.

(51) Int. Cl.
   *C07D 309/30* (2006.01)

(52) U.S. Cl. .................................................. 549/292

(58) Field of Classification Search .................. 549/292
   See application file for complete search history.

(56) References Cited

U.S. PATENT DOCUMENTS

| 4,444,784 A | 4/1984 | Hoffman et al. |
| 4,582,915 A | 4/1986 | Sleteinger et al. |
| 4,820,850 A | 4/1989 | Verhoeven et al. |
| 6,797,831 B2 | 9/2004 | Dandala et al. |
| 2002/0115712 A1 | 8/2002 | Szabo et al. |

FOREIGN PATENT DOCUMENTS

| EP | 0 351 918 B1 | 1/1990 |
| EP | 511 867 A1 | 11/1992 |
| EP | 0 864 560 A1 | 9/1998 |
| WO | WO 98/32751 | 7/1998 |
| WO | WO 00/53566 | 9/2000 |
| WO | WO 01/34590 A1 | 5/2001 |
| WO | WO 01/45484 A2 | 6/2001 |
| WO | WO 02/20451 A1 | 3/2002 |
| WO | WO 02/20457 A1 | 3/2002 |
| WO | WO 03/018570 A1 | 3/2003 |

*Primary Examiner*—Bernard Dentz
(74) *Attorney, Agent, or Firm*—Kenyon & Kenyon

(57) ABSTRACT

The present invention relates to a process for preparing simvastatin, wherein the simvastatin dimer content is controlled. More particularly, the present invention relates to a process for preparing simvastatin having a simvastatin dimer content of about 0.2 to about 0.4% wt. The present invention also relates to a process for preparing simvastatin having a simvastatin dimer content of less than about 0.2% wt. The present invention also discloses a commercial scale process of preparing simvastatin having a specified simvastatin dimer content which is reproducible.

23 Claims, No Drawings

PROCESS FOR PREPARING SIMVASTATIN HAVING CONTROLLED RANGES OF SIMVASTATIN DIMER CONTENT

CROSS-REFERENCE TO RELATED APPLICATIONS

This application claims the benefit of the U.S. Provisional Application Ser. Nos. 60/446,764 filed Feb. 11, 2003 and 60/463,065 filed Apr. 15, 2003, the disclosures of which are incorporated by reference in their entirety herein.

FIELD OF THE INVENTION

The present invention relates to a process for preparing simvastatin, wherein the simvastatin dimer content is controlled. More particularly, the present invention relates to a process for preparing simvastatin having a simvastatin dimer content of about 0.2 to about 0.4% wt. The present invention also relates to a process for preparing simvastatin having a simvastatin dimer content of less than about 0.2% wt. The present invention further relates to a commercial scale process for preparing the same.

BACKGROUND OF THE INVENTION

Simvastatin, a cholesterol-lowering agent, is chemically designated as butanoic acid, 2,2-dimethyl-1,2,3,7,8,8a-hexahydro-3,7-dimethyl-8-[2-(tetrahydro-4-hydroxy-6-oxo-2H-pyran-2-yl)ethyl]-1-napthalenyl ester, [1S-[1α,3α,7β,8β(2S*, 4S*),-8a β. Simvastatin dihydroxy acid is a competitive inhibitor of 3-hydroxy-3-methyl-glutaryl-coenzyme (HMG-CoA) reductase, which catalyzes the rate-limiting step conversion of HMG-CoA to mevalonate in cholesterol synthesis. Simvastatin is sold under the tradename ZOCOR® and is marketed by Merck & Co., Inc. There is a need for a high yield and efficient commercial scale processes for preparing simvastatin.

U.S. Pat. No. 4,444,784 describes heating the dihydroxy acid in neutral solvent with continuous removal of the water by-product in order to drive the equilibrium reaction toward lactone formation. However, heating promotes an undesirable esterification reaction between the 3-hydroxy group of the 3-hydroxylactone with the precursor free acid to increase the amount of dimer.

PCT/EP 98/00519 describes preparing simvastatin with a low level of dimer impurity. The lactonization process uses the ammonium salt of simvastatin as the starting material and involves refluxing in toluene followed by crystallizations to obtain pure simvastatin. The simvastatin prepared in accordance with this procedure is found to have a low dimer content of about 0.1 to about 0.12% wt.

Lactonization reaction of simvastatin ammonium salt to simvastatin is an equilibrium reaction which is illustrated as follows:

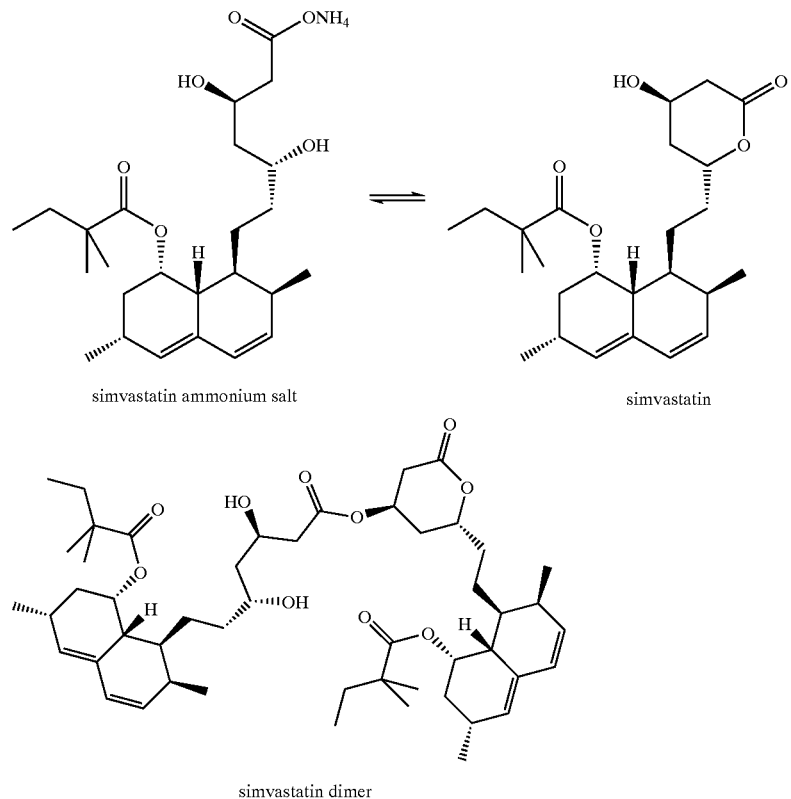

simvastatin dimer

Lactonization as an intramolecular esterification can be accompanied by the esterification of the reaction product with starting material present in the reaction mixture. This intermolecular esterification leads to the formation of simvastatin dimer byproduct having the structure shown in the scheme above.

The European and U.S. pharmaceutical industry standards for certain simvastatin products requires that simvastatin cannot contain more than 0.4% wt dimer. This relatively high amount of impurity accepted by pharmaceutical authorities may be due to the understanding that not only simvastatin but also the simvastatin dimer are precursors of the pharmacologically active dihydroxy open acid form of the compound (PCT/US 01/27466).

Efforts to produce simvastatin containing less than 0.2% of the simvastatin dimer have been made. EP 351 918 discloses a method for acid catalyzed lactonization leading to a simvastatin crude product containing less than 0.2% wt of simvastatin dimer. This reference discloses that attempts to produce simvastatin of this quality by purification had failed.

For other applications, it is desirable that purified simvastatin active ingredient contain about 0.2 to about 0.4% wt simvastatin dimer; more preferably, about 0.25 to about 0.34% wt. Accordingly, a reproducible process for preparing simvastatin active ingredient having a controllable dimer content in the specified ranges, as well as acceptable impurity profile, is desirable.

SUMMARY OF THE INVENTION

The present invention provides a process for preparing simvastatin, wherein the simvastatin dimer content is controlled.

In one embodiment, the present invention provides a process for preparing simvastatin with a specified simvastatin dimer content, comprising the steps of:
  a) lactonizing an ammonium salt of simvastatin in aromatic hydrocarbon at a concentration from about 25 to about 40 g/l to form a simvastatin;
  b) dissolving the simvastatin in at least one solvent selected from the group consisting of toluene, ethylacetate, tetrahydrofuran, and benzene and precipitating the dissolved simvastatin with an anti-solvent selected from the group consisting of pentane, hexane, heptane, cyclohexane and petroleum ether; and
  c) isolating the crystallized simvastatin, wherein the crystallized simvastatin contains a simvastatin dimer content of about 0.2 to about 0.4% wt.

Preferably, the concentration of the ammonium salt of simvastatin is from about 30 to about 35 g/l. More preferably, the concentration of the ammonium salt of simvastatin is about 35 g/l.

Preferably, the lactonizing step is performed by refluxing the ammonium salt of simvastatin in the aromatic hydrocarbon. Preferably, the aromatic hydrocarbon is selected from the group consisting of benzene, ethylbenzene, xylene and toluene. More preferably, the aromatic hydrocarbon is toluene.

Preferably, the lactonizing step is performed for about 3 to about 5 hours. More preferably, the lactonizing step is performed for 4 hours.

Preferably, the lactonizing step is performed in the presence of butyl hydroxytoluene.

Preferably, the crude simvastatin is dried. Preferably, the drying step is performed by evaporation. Preferably, the simvastatin is dried to residue.

Preferably, the crude simvastatin is dissolved in a solvent followed by precipitation. Preferably, the dissolving step is performed at about 60° C. Preferably, the precipitation is induced by adding an anti-solvent to the solution containing the dissolved simvastatin.

Preferably, the anti-solvent is at lease one solvent selected from the group of pentane, hexane, heptane, cyclohexane and petroleum ether.

Preferably, the process further comprises the steps of:
  d) dissolving the simvastatin obtained in step c) in a water miscible organic solvent selected from the group consisting of methanol, ethanol, acetone, acetonitrile and tetrahydrofuran; and
  e) adding an anti-solvent to induce precipitation to obtain recrystallized simvastatin.

Preferably, the recrystallization steps of d–e) are repeated. Preferably, the anti-solvent is water.

Preferably, the crystallized simvastatin contains a simvastatin dimer content of about 0.25 to about 0.34% wt.

In another embodiment, the present invention provides a process for preparing simvastatin with a specified simvastatin dimer content, comprising the steps of:
  a) lactonizing an ammonium salt of simvastatin in aromatic hydrocarbon at a concentration of less than about 60 g/l to form a simvastatin;
  b) dissolving the simvastatin in at least one solvent selected from the group consisting of toluene, ethylacetate, tetrahydrofuran, and benzene and precipitating the dissolved simvastatin with an anti-solvent selected from the group consisting of pentane, hexane, heptane, cyclohexane and petroleum ether;
  c) isolating the crystallized simvastatin;
  d) dissolving the crystallized simvastatin in at least one solvent selected from the group consisting of toluene, ethylacetate, tetrahydrofuran, and benzene and precipitating the dissolved simvastatin with an anti-solvent selected from the group consisting of pentane, hexane, heptane, cyclohexane and petroleum ether; and
  e) isolating the recrystallized simvastatin,
  wherein the recrystallized simvastatin contains a simvastatin dimer content of less than 0.2% wt.

Preferably, the concentration of the ammonium salt of simvastatin is less than about 40 g/l. More preferably, the concentration of the ammonium salt of simvastatin is about 35 g/l.

Preferably, the lactonizing step is performed by refluxing the ammonium salt of simvastatin in the aromatic hydrocarbon. Preferably, the aromatic hydrocarbon is selected from the group consisting of benzene, ethylbenzene, xylene and toluene. More preferably, the aromatic hydrocarbon is toluene.

Preferably, the lactonizing step is performed for about 3 to about 5 hours. More preferably, the lactonizing step is performed for 4 hours.

Preferably, the lactonizing step is performed in the presence of butyl hydroxytoluene.

Preferably, the crude simvastatin is dried. Preferably, the drying step is performed by evaporation. Preferably, the simvastatin is dried to residue.

Preferably, the dissolving step is performed at about 60° C. Preferably, the crystallizing step is performed by adding an anti-solvent to the solvent after simvastatin is dissolved. Preferably, the anti-solvent is at lease one solvent selected from the group pentane, hexane, heptane, cyclohexane and petroleum ether.

Preferably, the process further comprises the steps of:
  f) dissolving the simvastatin obtained in step e) in a water miscible organic solvent selected from the group consisting of methanol, ethanol, acetone, acetonitrile and tetrahydrofuran; and
  g) adding an anti-solvent to induce precipitation to obtain recrystallized simvastatin.

Preferably, the recrystallization steps of f–g) are repeated. Preferably, the anti-solvent is water.

Preferably, recrystallized simvastatin contains a simvastatin dimer content of less than about 0.19% wt.

In yet another embodiment, the present invention provides a commercial scale process for preparing simvastatin with a specified simvastatin dimer content, comprising the steps of:
   a) lactonizing an ammonium salt of simvastatin in aromatic hydrocarbon at a concentration from about 25 to about 40 g/l to form a simvastatin;
   b) dissolving the simvastatin in at least one solvent selected from the group consisting of toluene, ethylacetate, tetrahydrofuran, and benzene and precipitating the dissolved simvastatin with an anti-solvent selected from the group consisting of pentane, hexane, heptane, cyclohexane and petroleum ether; and
   c) isolating the crystallized simvastatin,
   wherein the crystallized simvastatin contains a simvastatin dimer content of about 0.2 to about 0.4% wt.

Preferably, the commercial scale process further comprises the steps of:
   d) dissolving the simvastatin obtained in step e) in a water miscible organic solvent selected from the group consisting of methanol, ethanol, acetone, acetonitrile and tetrahydrofuran; and
   e) adding an anti-solvent to induce precipitation to obtain recrystallized simvastatin.

Preferably, the recrystallization steps of f–g) are repeated. Preferably, the anti-solvent is water.

In yet another embodiment, the present invention provides a commercial scale process for preparing simvastatin with a specified simvastatin dimer content, comprising the steps of:
   a) lactonizing an ammonium salt of simvastatin in aromatic hydrocarbon at a concentration of less than about 60 g/l to form a simvastatin;
   b) dissolving the simvastatin in at least one solvent selected from the group consisting of toluene, ethylacetate, tetrahydrofuran, and benzene and precipitating the dissolved simvastatin with an anti-solvent selected from the group consisting of pentane, hexane, heptane, cyclohexane and petroleum ether;
   c) isolating the crystallized simvastatin;
   d) dissolving the crystallized simvastatin in at least one solvent selected from the group consisting of toluene, ethylacetate, tetrahydrofuran, and benzene and precipitating the dissolved simvastatin with an anti-solvent selected from the group consisting of pentane, hexane, heptane, cyclohexane and petroleum ether; and
   e) isolating the recrystallized simvastatin,
   wherein the recrystallized simvastatin contains a simvastatin dimer content of less than 0.2% wt.

Preferably, the commercial scale process further comprises the steps of:
   f) dissolving the simvastatin obtained in step e) in a water miscible organic solvent selected from the group consisting of methanol, ethanol, acetone, acetonitrile and tetrahydrofuran; and
   g) adding an anti-solvent to induce precipitation to obtain recrystallized simvastatin.

Preferably, the recrystallization steps of f–g) are repeated. Preferably, the anti-solvent is water.

DETAILED DESCRIPTION OF THE INVENTION

Definitions:

As used herein: "HMG-CoA reductase" refers to 3-hydroxy-3-methyl-glutarylcoenzyme A reductase; "an inhibitor of HMG-CoA reductase" refers to statins which can exists either as a 3-hydroxyl lactone ring or as the corresponding ring dihydroxy open acid; "RRT" refers to relative retention time (relative to that of simvastatin) of an impurity in HPLC; "RRT 0.68" refers to an impurity of simvastatin having a relative retention time of 0.68; "RRT 1.87" refers to the impurity of simvastatin dimer; "Lov" refers to lovastatin; "E-Lov" refers to epi-lovastatin; "Sim-OH-Ac" refers to dihydroxy open acid simvastatin; "Simv" refers to simvastatin; "Anhyd" refers to anhydrosimvastatin; "BHT" refers to butylhydroxytoluene; "DMBA" refers to dimethybutyric acid; "ammonium salt of simvastatin" includes the ammonium salt of 3,5-dihydroxy acid simvastatin; and, "commercial scale" refers to a simvastatin manufacturing process starting with at least about 100 gram (can be as high as hundreds of kilograms) of ammonium salt of simvastatin in the lactonization process.

"Anti-solvent" is generally known to the art to be a solvent, when added to a solution containing a dissolved solute, will induce the precipitation of the solute from the solution. "Water miscible organic solvent" refers to an organic solvent that is miscible with water.

Unless otherwise specified, "%" refers to % wt and "A %" refers to % area under HPLC. For the purposes of this application, "dimer" refers to simvastatin dimer, e.g., the ester of the 3-hydroxyl simvastatin lactone and free acid lactone precursor.

Without being bound by any theory or mechanism of the invention, it is believed that simvastatin formation is an intramolecular reaction and is independent of the concentration of the simvastatin ammonium salt in the reaction mixture. Simvastatin dimer formation, however, is an intermolecular reaction and can be accelerated by increasing the concentration of simvastatin salt in the reaction mixture.

The present invention provides a process for controlling simvastatin dimer content by lactonizing an ammonium salt of simvastatin at a specified concentration range. The concentration of ammonium simvastatin salt is less than about 60 g/l. Preferably, the concentration of ammonium simvastatin salt is about 25 to about 40 g/l. More preferably, the concentration of ammonium simvastatin salt is about 30 to about 35 g/l. Most preferably, the concentration of ammonium simvastatin salt is about 35 g/l.

Lactonization may be brought about by any means known in the art including thermal induction. Lactonization of ammonium salt of simvastatin at a concentration of about 20 g/l yields simvastatin which, after drying, results in a simvastatin containing about 0.50% to about 0.55% wt simvastatin dimer. Lactonization of ammonium salt of simvastatin at a concentration of about 30 to about 60 g/l yields increasing amount of simvastatin dimers in evaporated residues (0.7% to 1.2%; see Table 1).

The lactonizing step is preferably performed by refluxing the ammonium salt of simvastatin in aromatic hydrocarbon. Aromatic hydrocarbon includes, but not limited to, benzene, ethylbenzene, xylene, toluene and the like. Preferably, the aromatic hydrocarbon is toluene. Preferably, the lactonizing step is performed for about 3 to about 5 hours. More preferably, the lactonizing step is performed for 4 hours. Preferably, the lactonizing step is performed in the presence of butyl hydroxytoluene. Preferably, the crude simvastatin is dried. Preferably, the drying step is performed by evaporation. Preferably, the simvastatin is dried to residue.

The crude simvastatin is preferably dissolved in a solvent followed by precipitation. Preferably, the dissolving step is performed at about 60° C. Preferably, the precipitation is induced by adding an anti-solvent to the solution containing the dissolved simvastatin. Preferably, the anti-solvent is at lease one solvent selected from the group of pentane, hexane, heptane, cyclohexane and petroleum ether.

In addition to regulating the concentration of ammonium salt of simvastatin during the lactonization process, the present invention further provides another means for controlling simvastatin dimer content. The means involves purification of simvastatin using the steps of crystallization. According to the present invention, the process of controlling simvastatin dimer content may involve using a combination of the reaction conditions and crystallization strategy from different solvent systems.

One embodiment of the present invention involves crystallizing an evaporated solid residue of simvastatin derived from the lactonization reaction mixture. Preferably, the crystallization comprises the initial step of dissolving crude simvastatin in a crystallization solvent. Preferably, the solvent is at least one solvent selected from the group consisting of toluene, ethylacetate, tetrahydrofuran, and benzene. Precipitation may be induced by adding an anti-solvent to the solution. Preferably, an anti-solvent is exemplified, but not limited to, pentane, hexane, heptane, cyclohexane and petroleum ether.

Solution of crude simvastatin in toluene, ethylacetate, tetrahydrofuran and/or benzene followed by precipitation by addition of an anti-solvent (e.g., hexane) greatly reduce simvastatin dimer content. Such crystallization system is desirable for controlling simvastatin dimer at a specified range of less than about 0.2% wt. For example, a first crystallization of the evaporated simvastatin residue (obtained using simvastatin ammonium salt of about 30 g/l to about 60 g/l) from toluene-hexane mixture leads to crude simvastatin with a dimer content of about 0.3% to about 0.5% wt. (see Table 1).

A second crystallization of crude simvastatin from toluene-hexane mixture leads to purified simvastatin containing less than about 0.2%wt of simvastatin dimer (see Table 2).

Preferably, the apolar solvent-anti-solvent system uses toluene as an apolar solvent and hexane as an anti-solvent. More preferably, the ratio of toluene and hexane is 1:4 (v/v).

The recrystallization of crystallized simvastatin (e.g., crude simvastatin after crystallized with toluene-hexane) with a water miscible organic solvent does not change significantly the amount of simvastatin dimer. For example, a methanol solvent/water anti-solvent crystallization of either the crude simvastatin (obtained after the first toluene-hexane crystallization) or crystallized simvastatin (obtained after the second toluene-hexane crystallozation) has limited effect on dimer content; but, effectively removes other impurities. Therefore, final crystallization from methanol-water does not effect the amount of dimer.

Preferably, the water miscible organic solvent includes, but not limited to, methanol, ethanol, acetone, acetonitrile and tetrahydrafuran. Preferably, the crystallization solvent is ethanol or acetone. Most preferably, the crystallization solvent is methanol. Preferably, the anti-solvent used is water. Preferably, the polar solvent-anti-solvent system uses methanol as a polar solvent and water as an anti-solvent. More preferably, the ratio of methanol and water is 1:1 (v/v).

In accordance with the present invention, the lactonization using an ammonium salt of simvastatin of about 25 to 40 g/l followed by purification steps of toluene-hexane crystallization results in simvastatin containing a simvastatin dimer content of about 0.2 to about 0.4% wt.

In accordance with the present invention, the lactonization using an ammonium salt of simvastatin of less than 60 g/l followed by purification steps of repeated toluene/hexane crystallization results in simvastatin containing a simvastatin dimer content of less than 0.2% wt.

According to another embodiment, the present invention provides a commercial scale process by using ammonium salt of simvastatin of at least about 100 grams.

The simvastatin prepared according to the process of the invention contains a very low level of other impurities, typically less than about 0.1%.

The present invention will be more fully understood from the following examples. These examples are intended for illustration purposes, but do not in any way limit the scope of the invention.

EXAMPLES

Example 1

Effect of Varying Ammonium Simvastatin Concentrations on Simvastatin Impurity Profile a) Lactonization Simvastatin ammonium salt (9.0 grams) was refluxed in toluene (300 ml) for 2 hours under nitrogen in the presence of butylhydroxytoluene (BHT) (0.08 gram) using an oil bath for heating in a Dean—Stark condenser for removing water formed in the reaction. After reflux the reaction mixture was stirred at 85–90° C. for 3 hours. The reaction mixture was then evaporated to dryness to form a solid residue. The dimer in the simvastatin solid residue was 0.70% (see Table 1, exp. 3).

b) First Crystallization With Toluene-Hexane Solvent

Solid simvastatin residue was dissolved in toluene (20 ml) at about 60° C. The solution was treated with charcoal (0.3 gram), which was removed by filtration and was washed with toluene (4 ml). The solution was charged into a four-necked round bottom flask fitted with nitrogen inlet, thermometer, dropping funnel and reflux condenser. The solution was then heated to 58–62° C. and n-hexane (55 ml) was added dropwise at this temperature for 1 hour while stirring. The reaction mixture was then cooled to 0–5° C. in 1.5 hours and new portion of hexane (41 ml) was added to the slurry after 1 hour. The mixture was then stirred at this temperature for 1 additional hour. Product was collected, washed with the mixture of toluene (4 ml) and hexane (16 ml) containing BHT (0.007 gram) and dried at 48° C. in a vacuum oven to yield crude simvastatin. The dimer in the crude simvastatin was 0.32% (see Table 1, exp. 3).

Using the above lactonization conditions, we examined how varying concentrations of ammonium simvastatin salt affected the simvastatin impurity profile. Varying concentrations, 2% (exp. nos. 1–2), 3% (exp. no. 3), 4% (exp. no. 4), 6% (exp. no. 5) of ammonium simvastatin salt were tested. Lactonization was performed at reflux temperature of 3 hours (exp. no. 1) or 5 hours (exp. no. 2). The oil bath temperature was set at 125° C. (exp. no. 1) or 150° C. (exp. no. 6). Dimethybutyric acid (DMBA) (5% wt/wt) was added with ammonium simvastatin salt (exp. no. 7) to evaluate the effect of acid on simvastatin purity.

Table 1 summarizes the results of 20 to 60 g/l ammonium simvastatin salt concentration on the simvastatin impurity profile. As is evident in Table 1, increasing the concentration of the ammonium simvastatin salt from 20 to 60 g/l increases the amount of dimer, without significantly changing the amount of other impurities. Increasing lactonization temperature from 125° C. to 150° C. does not change the dimer content (exp. nos. 1 and 6), but addition of dimethyl butyric acid increases the dimer content (exp. nos. 1 and 7).

Example 2

Comparative a) Second Crystallization With Toluene-Hexane

Crude simvastatin, from exp. 5, in Table 1, was dissolved in toluene (20 ml) at about 60° C. and the solution was charged into a four-necked round bottomed flask fitted with nitrogen inlet, thermometer, dropping funnel and reflux condenser. The solution was then heated to 58–62° C. and n-hexane (46 ml) was added dropwise at this temperature for 1 hour while stirring. The reaction mixture was then cooled to 0–5° C. in 1.5 hours and new portion of hexane (34 ml) was added to the slurry in 1 hour. The mixture was then stirred at this temperature for 1 additional hour. Product was collected, washed with the mixture of toluene (3 ml) and hexane (12 ml) containing BHT (0.007 gram) and dried at 48° C. in a vacuum oven to yield a purified simvastatin (exp. 5a).

b) Third Crystallization With Methanol-Water

Purified simvastatin from the second toluene-hexane crystallization was dissolved in methanol (49 ml), treated with charcoal (0.25 gram) which was filtered. The purified simvastatin was washed with methanol (15 ml). BHT (0.004 gram) and water (23 ml) were added to the solution, which was then heated to 35–40° C. while stirring. The solution was cooled to 13–17° C. gradually in 2 hours. Precipitation began at about 30° C. The suspension was then heated to 35–40° C. again to dissolve most of the crystals. New portion of water (46 ml) was then added dropwise at 35–40° C. in 45–50 min and the slurry was stirred for 1 hour at this temperature, then cooled to 5–10° C. in 2 hours and stirred at this temperature for 1 hour. The resulting crystalline material was collected, washed with the mixture of water (7 ml) and methanol (6 ml) and dried at 48° C. for a night in a vacuum oven to provide the simvastatin final product (exp. 5b).

Table 2 summarizes the results of the second toluene/hexane crystallization (exp. 5a) followed by a methanol/water crystallization (exp. 5b) steps on the simvastatin impurity profile. As is evident in Table 2, a second toluene-hexane crystallization step significantly decreases dimer from 0.48% to 0.19% and a third methanol/water crystallization step does not further significantly reduce dimer (0.18%) (see Table 2). The methanol-water crystallization does not significantly affect the dimer content but efficiently removes polar impurities, (e.g., RRT=0.58 and RRT=0.76 (simvastatin hydroxy acid).

Example 3

Different Simvastatin Ammonium Salt Starting Material

The experiments described above (Examples 1 to 7) used recrystallized simvastatin ammonium salt as starting material. Since impurities of the starting ammonium salt can also influence the impurity profile of the simvastatin product, this effect was also studied.

Recrystallized simvastatin ammonium salt starting material from a laboratory batch and crude simvastatin ammonium salt from commercial production were used and the lactonization and crystallization steps were performed as in Example 1.

The impurity profile of crude simvastatin obtained from different quality simvastatin ammonium salt (i.e., (1) laboratory ammonium simvastatin salt described above, and (2) production plant ammonium simvastatin salt) are summarized in Table 3. Table 3 summarizes the impurity profile of the crude simvastatin (i.e., obtained after first toluene/hexane crystallization) prepared from the simvastatin ammonium salt from laboratory batch or commercial production. As evident in Table 3, the quality of the ammonium salt does not effect the amount of the dimer in the crude simvastatin. As also evident in Table 3 that the amount of other impurities can depend on the purity of the ammonium salt.

Example 4

Effect of Repeated Methanol-Water Crystallization on Impurity Profile

The crude simvastatin products described in Table 3 were subjected to repeated methanol-water crystallizations, after the toluene/hexane crystallization of Example 3, to yield the final product. The yield, assay and impurity profile of the products are summarized in Table 4.

Changing the crystallization steps affects the impurity profile of the final product. The second toluene-hexane crystallization (see example 2) effectively removed both polar (RRT=0.68, simvastatin hydroxy acid) and apolar (RRT=1.40) impurities (see Table 2) and dimer. The data in Table 4 shows that methanol-water crystallization does not significantly affect the dimer content but efficiently removes the polar impurities (e.g., RRT=0.68 and RRT=0.76 (simvastatin hydroxyl acid).

Example 5

Scaled-up Process for Preparing Simvastatin

The procedure elaborated in the foregoing examples; i.e., 10 gram scale was scaled-up in the laboratory to 100 gram scale using a 4 L jacketed reactor instead of round bottomed flasks. A process for preparing simvastatin starting from 105.0 grams ammonium salt of commercial production plant origin is set forth below:

Step a) Lactonization Process

Simvastatin ammonium salt (105.0 grams) was stirred at reflux temperature (109–111° C.) in toluene (3,000 ml) for 2 hours under nitrogen in the presence of butylhydroxytoluene (BHT) (0.8 gram) in a 4 L jacketed reactor fitted with nitrogen inlet, thermometer in a Dean-Stark condenser for removing of water formed in the reaction. After reflux, the reaction mixture was stirred at 85–90° C. for 3 hours. The reaction mixture was then evaporated to dryness to form a solid residue (exp. no. 15, Table 5).

Step b) Preparation of Crude Simvastatin

Evaporation residue (112.0 grams) was dissolved in toluene (370 ml) at about 60° C. The solution was treated with charcoal (5.0 grams) which was removed by filtration and washed with toluene (50 ml). The solution was charged into a four-necked round bottom flask fitted with nitrogen inlet, thermometer, dropping funnel and reflux condenser. The solution was then heated to 58–62° C. and n-hexane (968 ml) was added dropwise at this temperature for 1 hour while stirring. The reaction mixture was then cooled to 0–5° C. in 1.5 hours and new portion of n-hexane (712 ml) was added to the slurry in 1 hour. The mixture was then stirred at this temperature for an additional 1 hour. The product was collected, washed with the mixture of toluene (60 ml) and hexane (240 ml) containing BHT (0.13 gram) and dried at 48° C. in a vacuum oven to yield 89.0 grams of crude simvastatin (exp. no. 16, Table 5).

Separation of Crude Simvastatin

Crude simvastatin was divided into two equal parts. One part was subjected to one toluene-hexane recrystallization followed by a methanol-water final crystallization according to one purification strategy, the other part was subjected to a methanol-water recrystallization followed by a methanol-water final crystallization according to an alternative purification strategy.

Purification Strategy of Applying Toluene-hexane Recrystallization Followed by Methanol-water Final Crystallization Step c) Purification by Toluene-Hexane Recrystallization Crude simvastatin ((43.75 grams) from step b) was dissolved in toluene (150 ml) at about 60° C., treated with charcoal (2.25 grams) which was washed with toluene (24 ml). The filtrate was charged into a four-necked round-bottom flask fitted with nitrogen inlet, thermometer, dropping funnel and reflux condenser. The solution was then heated to 58–62° C. and n-hexane (400 ml) was added dropwise at this temperature for 1 hour while stirring. The reaction mixture was then cooled to 0–5° C. in 1.5 hour and a new portion of hexane (296 ml) was added to the slurry in 1 hour. The mixture was then stirred at this temperature for an additional 1 hour. The product was collected, washed with a mixture of toluene (29 ml) and hexane (116 ml) containing BHT (0.067 gram), and dried at 48° C. in a vacuum oven to yield 42.5 gram of purified simvastatin (exp. no. 17, Table 5).

Step d) Methanol-Water Final Crystallization

Purified simvastatin (41.0 grams) from step c) was dissolved in methanol (438 ml), treated with charcoal (2.25 grams) which was filtered and washed with methanol (137 ml). BHT (0.033 gram) and water (203 ml) were added to the solution, which was heated to 35–40° C. while stirring. The solution was cooled to 13–17° C. gradually in 2 hours. Precipitation began at about 30° C. The suspension was then heated to 35–40° C. again to dissolve most of the crystals and an additional portion of water (415 ml) was then added dropwise at 35–40° C. in 45–50 min. The slurry was stirred for 1 hour at this temperature, then was cooled to 5–10° C. in 2 hours and stirred at this temperature for 1 hour. Crystalline material was collected, washed with the mixture of water (61 ml) and methanol (54 ml) and dried at 48° C. for a night in a vacuum oven to afford 39.16 grams of simvastatin final product (exp. no. 18, Table 5).

Purification Strategy of Applying Methanol-water Recrystallization Followed by Methanol-water Final Crystallization Step e) Purification by First Methanol-Water Crystallization Another portion of the crude from step b) crude simvastatin (43.75 grams) was dissolved in was dissolved in methanol (438 ml), treated with charcoal (2.25 grams) which was filtered and washed with methanol (137 ml). BHT (0.033 gram) and water (203 ml) were added to the solution and then it was heated to 35–40° C. while stirring. The solution was cooled to 13–17° C. gradually in 2 hours. Precipitation begins at about 30° C. The suspension was then heated to 35–40° C. again to dissolve most of the crystals and new portion of water (415 ml) was then added dropwise at 35–40° C. in 45–50 min. The slurry was stirred for 1 hour at this temperature then was cooled to 5–10° C. in 2 hours and stirred at this temperature for 1 hour. Crystalline material was collected, washed with the mixture of water (61 ml) and methanol (54 ml) and dried at 48° C. for a night in a vacuum oven to yield 42.5 grams of simvastatin final product (exp. no.19, Table 5).

Toluene (150 ml) at about 60° C., treated with charcoal (2.25 grams) which was washed with toluene (24 ml). The filtrate was charged into a four-necked round bottomed flask fitted with nitrogen inlet, thermometer, dropping funnel and reflux condenser. The solution was then The data in Table 6 show that scaling-up the process (e.g., commercial process), when using about 3.5% ammonium salt simvastatin followed by crystallization of the crude simvastatin with a first methanol/water solvent results in simvastatin with the specified range of dimer content (see, exp. 19, Table 5).

Step f) Purification by Second Methanol-Water Crystallization

Purified simvastatin (41.0 grams) from step e) was dissolved in methanol (438 ml), treated with charcoal (2.25 grams) which was filtered and washed with methanol (137 ml). BHT (0.033 grams) and water (203 ml) were added to the solution then it was heated to 35–40° C. while stirring. The solution was cooled to 13–17° C. gradually in 2 hours. Precipitation begins at about 30° C. The suspension was then heated to 35–40° C. again to dissolve most of the crystals and new portion of water (415 ml) was then added dropwise at 35–40° C. in 45–50 min. The slurry was stirred for 1 hour at this temperature then was cooled to 5–10° C. in 2 hours and stirred at this temperature for 1 hour. Crystalline material was collected, washed with the mixture of water (61 ml) and methanol (54 ml) and dried at 48° C. for a night in a vacuum oven to afford 39.55 grams of simvastatin final product.

The data in Table 5 also show that a second methanol/water crystallization results in simvastatin with the specified range of dimer content (see, exp. 20, Table 5).

The present invention is not to be limited in scope by the specific embodiments described herein. It will be understood that various modifications may be made without departing from the spirit and scope of the invention. Various publications and patents are cited herein, the disclosures of which are incorporated by reference in their entireties.

TABLE 1

Effect of the Lactonization Conditions on Impurity Profile of Crude Simvastatin

| Exp. No. | Conditions | Dimer in Solid Residue | Yield (%) | [0.68] | [0.76] Sim-OH—Ac | [0.86] Lov | [0.88] E-Lov | Simv | [1.40] Anhyd | [1.87] Dimer |
|---|---|---|---|---|---|---|---|---|---|---|
| 1 | Conc. 2%[a] | 0.55 | 91 | 0.04 | 0.43 | 0.11 | 0.05 | 98.94 | 0.02 | 0.24 |
| 2 | Conc. 2%[b] | 0.51 | 91 | 0.04 | 0.22 | 0.09 | 0.04 | 99.14 | 0.04 | 0.23 |
| 3 | Conc. 3% | 0.70 | 90 | 0.04 | 0.33 | 0.08 | 0.046 | 98.93 | 0.04 | 0.32 |
| 4 | Conc. 4% | 0.91 | 93 | 0.04 | 0.59 | 0.10 | 0.05 | 98.53 | 0.02 | 0.43 |
| 5 | Conc. 6% | 1.2 | 93 | 0.04 | 0.18 | 0.09 | 0.05 | 98.92 | 0.05 | 0.48 |
| 6 | Conc. 2% Higher oil bath temperature[c] | 0.58 | 93 | 0.05 | 0.47 | 0.11 | 0.05 | 98.84 | 0.03 | 0.26 |
| 7 | Conc. 2% Added DMBA[d] | 0.94 | 84 | 0.04 | 0.73 | 0.11 | 0.05 | 97.76 | 0.63 | 0.45 |

[a]laboratory procedure for lactonization described above, the oil bath temperature was 125° C.
[b]lactonization was performed at a reflux temperature for 5 hours
[c]the oil bath temperature was 150° C.
[d]DMBA (5% wt/wt) was added with ammonium simvastatin salt to the reaction mixture

TABLE 2

Crystallization of the Crude Simvastatin Obtained in Exp. No. 5 (in Table 1)

| Exp. No. | Conditions | Yield (%) | [0.68] | [0.76] Sim-OH—Ac | [0.86] Lov | [0.88] E-Lov | Simv | [1.40] Anhyd | [1.87] Dimer |
|---|---|---|---|---|---|---|---|---|---|
| 5a | 2nd Toluene-Hexane cryst. | 95 | 0.03 | 0.06 | 0.09 | 0.05 | 99.46 | — | 0.19 |
| 5b | Methanol-water cryst. | 94 | — | — | 0.09 | 0.04 | 99.51 | 0.01 | 0.18 |

TABLE 3

Characterization of Lactonisation and Crude Simvastatin starting from Different Quality of Simvastatin Ammonium Salt

| Exp. No. | Conc. | Dimer in Solid Res. | Yield (%) | [0.68] | [0.76] Simv-OH—Ac | [0.86] Lov | [0.88] E-Lov | Simv | [1.40] Anhyd | [1.87] Dimer |
|---|---|---|---|---|---|---|---|---|---|---|
| 8[a] | 3% | 0.61 | 90 | 0.03 | 0.26 | 0.13 | 0.04 | 99.09 | 0.03 | 0.26 |
| 9[a] | 3% | 0.54 | 84 | — | 0.23 | 0.09 | 0.04 | 98.03 | 0.16 | 0.24 |
| 10[a] | 3.5% | 0.83 | 89 | 0.04 | 0.22 | 0.08 | 0.04 | 98.98 | 0.03 | 0.33 |
| 11[a] | 3.5% | 0.75 | 91 | 0.03 | 0.29 | 0.08 | 0.03 | 99.01 | 0.03 | 0.30 |
| 12[b] | 3.5% | 0.80 | 89 | 0.20 | 0.15 | 0.17 | 0.08 | 98.78 | 0.03 | 0.32 |
| 13[b] | 3.5% | 0.78 | 90 | 0.25 | 0.19 | 0.18 | 0.09 | 98.44 | 0.04 | 0.33 |

[a]starting from recrystallized ammonium salt of simvastatin from laboratory batches
[b]starting from recrystallized ammonium salt of simvastatin from commercial production plant

TABLE 4

Characterization of Impurity Profile in Simvastatin Obtained After First and/or Second Methanol-Water Crystallization

| Exp. No. [recryst] | Yield (%) | Assay (%) | [0.68] | [0.76] Simv-OH—Ac | [0.86] Lov | [0.88] E-Lov | [1.40] Anhyd | [1.87] Dimer |
|---|---|---|---|---|---|---|---|---|
| 8 [2nd] | 96 | 100.5 | 0.00 | 0.00 | 0.09 | 0.04 | 0.03 | 0.24 |
| 9 [2nd] | 94 | 100.1 | 0.00 | 0.04 | 0.09 | 0.05 | 0.15 | 0.22 |
| 10 [1st] | 93 | 99.5 | 0.00 | 0.00 | 0.08 | 0.04 | 0.03 | 0.30 |
| 10 [2nd] | 94 | 99.2 | 0.00 | 0.00 | 0.08 | 0.04 | 0.04 | 0.28 |
| 11 [1st] | 93 | 99.8 | 0.00 | 0.01 | 0.08 | 0.05 | 0.03 | 0.27 |
| 11 [2nd] | 93 | 99.9 | 0.00 | 0.00 | 0.08 | 0.04 | 0.03 | 0.26 |
| 12 [1st] | 95 | 100.1 | 0.06 | 0.00 | 0.12 | 0.08 | 0.03 | 0.26 |
| 12 [2nd] | 95 | 100.6 | 0.01 | 0.00 | 0.12 | 0.08 | 0.03 | 0.25 |
| 13 [1st] | 95 | 100.7 | 0.08 | 0.02 | 0.13 | 0.08 | 0.04 | 0.28 |
| 13 [2nd] | 94 | 100.1 | 0.01 | 0.00 | 0.13 | 0.08 | 0.04 | 0.26 |

[1st] refers to first crystallization from Methanol-Water
[2nd] refers to second crystallizations (i.e., repeated crystallization) from Methanol-Water

TABLE 5

Impurity Profile at Different Stages of Lactonization and Purification of Scaled-Up Product

| Exp. No. | Stage | Yield (%) | Assay (%) | [0.68] | [0.76] Sim-OH—Ac | [0.86] Lov | [0.88] E-Lov | Simv | [1.40] Anhyd | [1.87] Dimer |
|---|---|---|---|---|---|---|---|---|---|---|
| 14 | End of the lact. | | | 0.46 | 1.60 | 0.02 | 0.01 | 95.8 | 0.26 | 0.67 |
| 15 | Evap. solid res. | | | 0.48 | 1.14 | 0.06 | 0.02 | 96.1 | 0.26 | 0.73 |
| 16 | Crude simv. | 91.8 | | 0.18 | 0.20 | 0.07 | 0.04 | 98.8 | 0.04 | 0.30 |
| 17 | Recrystallization from toluene-hexane | 97.1 | | 0.07 | 0.07 | 0.07 | 0.07 | 99.5 | 0.00 | 0.11 |
| 18 | Recrystallization from methanol-water | 95.5 | | 0.02 | 0.00 | 0.07 | 0.04 | 99.7 | 0.00 | 0.11 |
| 19 | 1$^{st}$ crystallization from methanol-water | 97.1 | 97.0 | 0.04 | 0.00 | 0.07 | 0.04 | 98.4 | 0.04 | 0.31 |
| 20 | 2$^{nd}$ crystallization from methanol-water | 96.5 | 99.0 | 0.01 | 0.00 | 0.07 | 0.04 | 99.5 | 0.04 | 0.28 |

What is claimed is:

1. A process for preparing simvastatin with a specified simvastatin dimer content, comprising the steps of:
   a) lactonizing an ammonium salt of simvastatin in aromatic hydrocarbon at a concentration of less than about 60 g/l to form a simvastatin;
   b) dissolving the simvastatin in at least one solvent selected from the group consisting of toluene, ethylacetate, tetrahydrofuran, and benzene and precipitating the dissolved simvastatin with an anti-solvent selected from the group consisting of pentane, hexane, heptane, cyclohexane and petroleum ether;
   c) isolating the crystallized simvastatin;
   d) dissolving the crystallized simvastatin in at least one solvent selected from the group consisting of toluene, ethylacetate, tetrahydrofuran, and benzene and precipitating the dissolved simvastatin with an anti-solvent selected from the group consisting of pentane, hexane, heptane, cyclohexane and petroleum ether; and
   e) isolating the recrystallized simvastatin,
   wherein the recrystallized simvastatin contains a simvastatin dimer content of less than 0.2% wt.

2. The process of claim 1, wherein the steps d) and e) are repeated.

3. The process of claim 1, wherein the concentration of the ammonium salt of simvastatin is from about 30 to about 35 g/l.

4. The process of claim 3, wherein the concentration of the ammonium salt of simvastatin is about 35 g/l.

5. The process of claim 1, wherein the lactonizing step is performed by refluxing the ammonium salt of simvastatin in the aromatic hydrocarbon.

6. The process of claim 5, wherein the aromatic hydrocarbon is selected from the group consisting of benzene, ethylbenzene, xylene and toluene.

7. The process of claim 5, wherein the aromatic hydrocarbon is toluene.

8. The process of claim 5, wherein the lactonizing step is performed for about 3 to about 5 hours.

9. The process of claim 8, wherein the lactonizing step is performed for 4 hours.

10. The process of claim 1, wherein the lactonizing step is performed in the presence of butyl hydroxytoluene.

11. The process of claim 1, after step a) and before step b), further comprising the step of drying the simvastatin obtained in step a).

12. The process of claim 11, wherein the drying step is performed by evaporation.

13. The process of claim 11, wherein the simvastatin obtained in step a) is dried to residue by drying.

14. The process of claim 11, wherein the dissolving step in b) or d) is performed at about 60° C.

15. The process of claim 1, after step e), further comprises the steps of:
   f) dissolving the simvastatin obtained in step e) in a water miscible organic solvent selected from the group consisting of methanol, ethanol, acetone, acetonitrile and tetrahydrofuran; and
   g) adding an anti-solvent to induce precipitation to obtain recrystallized simvastatin.

16. The process of claim 15, wherein the steps f–g) are repeated.

17. The process of claim 15, wherein the water miscible organic solvent is methanol.

18. The process of claim 15, wherein the anti-solvent is water.

19. The process of claim 1, wherein the crystallized simvastatin contains a simvastatin dimer content of less than about 0.19% wt.

20. A process for preparing simvastatin with a specified simvastatin dimer content, comprising the steps of:
   a) lactonizing an ammonium salt of simvastatin in toluene at a concentration of less than about 60 g/l to form a simvastatin;
   b) dissolving the simvastatin in toluene and precipitating the dissolved simvastatin with hexane;
   c) isolating the crystallized simvastatin;
   d) dissolving the crystallized simvastatin intoluene and precipitating the dissolved simvastatin with hexane; and
   e) isolating the recrystallized simvastatin,
   wherein the recrystallized simvastatin contains a simvastatin dimer content of less than 0.2% wt.

21. The process of claim 20, wherein the steps d) and e) are repeated.

22. The process of claim 20, after step e) further comprises the steps of:
   f) dissolvieng the simvastatin obtained in step e) in methanol; and
   g) adding water to induce precipitation to obtain recrystallized simvastatin.

23. A process for preparing simvastatin as in claim 1, wherein the ammonium salt of simvastatin is at least about 100 grams.

* * * * *